United States Patent
O'Sullivan

(10) Patent No.: US 6,746,672 B2
(45) Date of Patent: Jun. 8, 2004

(54) **ISOLATED BIFIDOBACTERIA THAT PRODUCE SIDEROPHORES WHICH INHIBIT GROWTH OF *LACTOCOCCUS LACTIS***

(75) Inventor: Daniel J. O'Sullivan, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/884,894

(22) Filed: Jun. 19, 2001

(65) Prior Publication Data

US 2002/0058326 A1 May 16, 2002

Related U.S. Application Data

(60) Provisional application No. 60/212,273, filed on Jun. 19, 2000.

(51) Int. Cl.$^7$ .......................... A01N 63/00; C12N 1/00; C12N 1/12; C12N 1/20
(52) U.S. Cl. .................... 424/93.4; 435/252.1; 435/822
(58) Field of Search .................... 435/243, 252.1, 435/822; 514/1; 424/93.4

(56) References Cited

U.S. PATENT DOCUMENTS

| | | | |
|---|---|---|---|
| 2,785,108 A | | 3/1957 | Hawley |
| 2,935,503 A | | 5/1960 | Hawley |
| 4,087,559 A | * | 5/1978 | Mutai et al. .................. 426/43 |
| 4,091,117 A | | 5/1978 | Mutai et al. |
| 4,716,115 A | | 12/1987 | Gonzalez et al. |
| 5,173,297 A | | 12/1992 | Vedamuthu et al. |
| 5,294,458 A | | 3/1994 | Fujimori |
| 5,340,577 A | | 8/1994 | Nisbet et al. |
| 5,494,664 A | | 2/1996 | Brassart et al. |
| 5,520,936 A | | 5/1996 | Delespaul et al. |
| 5,594,103 A | | 1/1997 | De Vos et al. |
| 5,602,109 A | | 2/1997 | Masor et al. |
| 5,700,590 A | | 12/1997 | Masor et al. |
| 5,753,614 A | | 5/1998 | Blackburn et al. |
| 5,776,524 A | | 7/1998 | Reinhart |
| 5,837,238 A | | 11/1998 | Casas et al. |
| 5,877,272 A | | 3/1999 | Vandenbergh |
| 5,902,578 A | | 5/1999 | Halpin-Dohnalek et al. |
| 5,902,743 A | | 5/1999 | Luchansky et al. |
| 5,922,375 A | | 7/1999 | Luchansky et al. |
| 5,952,314 A | | 9/1999 | DeMichele et al. |
| 5,968,569 A | | 10/1999 | Cavadini et al. |
| 5,972,415 A | | 10/1999 | Brassart et al. |
| 6,077,824 A | * | 6/2000 | English et al. .................. 514/12 |

OTHER PUBLICATIONS

Wun et al. "A New Procedure to Enhance fhuF Expression...", May 24, 2000, Amer. Soc. for Microb., pp. 411.*
Rambaud et al, "Dairy Products and intestinal flora", Dairy Proudcts in Human Helath and Nutrition, Rios et al (eds) 1994, see pages 389–399.*

Kullen et al., "Differentiation of Ingested and Endogenous Bifidobacteria by DNA Fingerprinting Demonstrates the Survival of an Unmodified Strain in the Gastrointestinal Tract of Humans," *American Society for Nutritional Sciences*, 1997:89–94.

Kullen et al., "Evaluation of using a short region of the recA gene for rapid and sensitive speciation of dominant bifidobacteria in the human large intestine," *FEMS Microbiology Letters.*, 1997; 154:377–383.

Bezkorovainy et al., "Iron Metabolism in Bifidobacteria," *Int. Dairy Journal 6*, 1996; 6(10):905–919.

Bezkorovainy et al., "Aspects of Iron Metabolism in *Bifidobacterium Bifidum* Var. *Pennsylvanicus*," *Int. J. Biochem.*, 1983; 15(3):361–366.

Topouzian et al., "Iron uptake by *Bifidobacterium bifidum* var. *pennsylvanicus*: the effect of sulfhydryl reagents and metal chelators," *IRCS Med. Sci.*, 1986, 14(3):275–276.

American Type Culture Collection, "ATCC No. 9341," organism: *Micrococcus luteus* (*Schroeter*); designation: FDA strain PCI 1001 [online]; Manassas, VA [retrieved on Apr. 3, 2002] from the Internet. Retrieved from the Internet: <URL: http://phage.atcc.org/cgi–bin/searchengine/longview.cgi?view=ba,534636,9341&text=9341>; 2 pgs.

American Type Culture Collection, "ATCC No. 29425," organism: *Escherichia coli* (*Migula*); designation: K12 [online]; Manassas, VA [retrieved on Apr. 3, 2002] from the Internet. Retrieved from the Internet: <URL: http://phage.atcc.org/cgi–bin/searchengine/longview.cgi?view=ba,5225109,29425&text=k12>; 1 pg.

Anderssen et al., "Antagonistic activity of *Lactobacillus plantarum* C11: two new two–peptide bacteriocins, plantaricins EF and JK, and the induction factor plantaricin A," *Appl. Environ. Microbiol.*, 64(6):2269–2272 (Jun. 1998).

Archibald, "*Lactobacillus plantarum*, and organism not requiring iron," *FEMS Microbiol. Letts.*, 19:29–32 (1983).

Bezkorovainy, "Iron transport an utilization by bifidobacteria," In *Biochemistry and Physiology of Bifidobacteria*, Bezkorovainy et al., eds; CRC Press, Inc., Boca Raton, FL; pp. 147–176 (1989).

Bollag et al., *Protein Methods*, Wiley and Sons, Inc., New York, NY; title page, publisher's page and table of contents—10 pgs. (1996).

(List continued on next page.)

*Primary Examiner*—David M. Noff
*Assistant Examiner*—Deborah K. Ware
(74) *Attorney, Agent, or Firm*—Mueting, Raasch & Gebhardt, P.A.

(57) ABSTRACT

Isolated Bifidobacterium strains are obtained that secrete a siderophore that inhibits the growth of microbes in the gastrointestinal tract of an animal. Microbes inhibited include *Lactococcus lactis, Clostridium difficile*, and *Clostridium perfringens*. The Bifidobacterium or siderophore isolated from the Bifidobacterium can be administered to an animal. The Bifidobacterium is grown under iron limiting conditions when obtaining the siderophore. Microbes are inhibited by the siderophore binding iron.

18 Claims, No Drawings

OTHER PUBLICATIONS

Braun "Effect of consumption of human milk and other formulas on intestinal bacterial flora in infants," Chapter 23 in *Textbook of Gastroenterology and Nutrition in Infancy*, Raven Press, New York, NY; pp. 247–253 (1981).

Breed et al., *Bergey's Manual of Determinative Bacteriology*, 7th Edition. The Williams and Wilkins Co., Baltimore, MD; title page, publisher's page, and table of contents only—8 pages (1957).

de Ruyter et al., "Functional analysis of promoters in the nisin gene cluster of *Lactococcus lactis*," *J. Bacteriol.*, 178(12):3434–3439 (Jun. 1996).

Dodd et al., "Analysis of the genetic determinant for production of the peptide antibiotic nisin," *J. Gen. Microbiol.*, 136(Pt 3):555–566 (Mar. 1990).

Eijsink et al., "Induction of bacteriocin production in *Lactobacillus sake* by a secreted peptide," *J. Bacteriol.*, 178(8):2232–2237 (Apr. 1996).

Engelke et al., "Biosynthesis of the lantiobiotic nisin: genomic organization and membrane localization of the NisB protein," *Appl. Environ. Microbiol.*, 58(11)3730–3743 (Nov. 1992).

Engelke et al., "Regulation of nisin biosynthesis and immunity in *Lactococcus lactis* 6F3," *Appl. Environ. Microbiol.*, 60(3):814–825 (Mar. 1994).

Fuller, R., "Probiotics in man and animals," *J Appl Bacteriol.*, 66(5):365–378 (May 1989).

Fuller, R., "Probiotics for farm animals," In *Probiotics: A Critical Review*, Tannock, ed., Horizon Scientific Press, Wymondham, UK; pp. 15–22 (1999).

Green, "Case report: fatal anaerobic pulmonary infection due to *Bifidobacterium eriksonii*," *Postgrad Med.* 1978 Mar;63(3):187–8, 190, 192.

Gibson et al., "Regulatory effects of bifidobacteria on the growth of other colonic bacteria," *J Appl Bacteriol.*, 77(4):412–420 (Oct. 1994).

Hansen, "Nisin as a model food preservative," *Crit Rev Food Sci Nutr.*, 34(1):69–93 (1994).

Ibrahim et al., "Inhibition of *Escherichia coli* by bifidobacteria," *J. Food Prot.*, 56(8):713–715 (Aug. 1993).

Immonen et al., "The codon usage of the *nisZ* operon in *Lactococcus lactis* N8 suggests a non–lactococcal origin of the cojugative nisin–sucrose transposon," *DNA Seq.*, 5(4):203–218 (1995).

Klaenhammer, "Genetics of bacteriocins produced by lactic acid bacteria," *FEMS Microbiol. Rev.*, 12(1–3):39–85 (Sept. 1993).

Kuipers et al., "Characterization of the nisin gene cluster *nisABTCIPR* of *Lactococcus lactis*. Requirement of expression of the *nisA* and *nisI* genes for development of immunity," *Eur. J. Biochem.*, 216(1):281–291 (Aug. 1993).

Kuipers et al., "Autoregulation of nisin biosynthesis in *Lactococcus lactis* by signal transduction," *J. Biol. Chem.*, 270(45):27299–27304 (Nov. 1995).

Kullen et al., "Evaluation of using a short region of the *recA* gene for rapid and sensitive specification of dominant bifidobacteria in the human large intestine," *FEMS Microbiol. Lett.*, 154(2):377–383 (Sep. 1997).

Mevissen–Verhage et al., "Effect of iron on neonatal gut flora during the first three months of life," *Eur. J. Clin. Microbiol.*, 4(3):273–278 (Jun. 1985).

Mitsuoka et al., "Ecology of the bifidobacteria," *American Journal of Clinical Nutrition.* 1977 Nov.;30(11):1799–1810.

Modler et al. "Bifidobacteria and bifidogenic factors," *Canadian Institute of Food Science Technology Journal* 1990; 23(1):29–41.

Muñoa et al., "Selective medium for isolation and enumeration of Bifidobacterium spp," *Appl. Environ. Microbiol.*, 54(7):1715–1718 (Jul. 1988).

Neilands, "Molecular aspects of regulation of high affinity iron absorption in microorganisms," Chapter 3 in *Metal–Ion Induced Regulation of Gene* Expression, which is vol. 8 of series *Adv. Inorg. Biochem.*, pp. 63–90 (1990).

Neilands et al. "Comparative biochemistry of microbial iron assimilation," In *Iron Transport in Microbes, Plants, Animals*, Winkelmann et al., eds.; VCH mbh, Weinheim, Germany, pp. 3–33 (1987).

Nes et al., "Biosynthesis of bacteriocins in lactic acid bacteria," *Antonie Van Leeuwenhoek*, 70(2–4):113–128 (Oct. 1996).

Nilsen et al., "An exported inducer peptide regulates bacteriocin production in *Enterococcus faecium* CTC492," *J. Bacteriol.*, 180(7):1848–1854 (Apr. 1998).

O'Sullivan, "Cloning, organization and regulation of genes involved in iron metabolism in fluorescent Pseudomonas spp. with biocontrol potential," Ph.D. thesis, National University of Ireland, Cork; pp. 1–120 (1990).

O'Sullivan et al., "Traits of fluorescent Pseudomonas spp. involved in suppression of plant root pathogens," *Microbiol. Rev.*, 56(4):662–676 (Dec. 1992).

O'Sullivan et al., "Tracking of probiotic bifidobacteria in the intestine," *Int. Dairy J.*, 8:513–525 (1998).

O'Sullivan "Characterization of non–acid inhibitory characteristics of a human Bifidobacterium isolate against clostridia and *E. coli*," American Dairy Science Association 1999 Annual Meeting, Memphis Cook Convention Center, Memphis, TN, Jun. 20–23, 1999 (abstract available Jun. 19, 1999).

O'Sullivan, "Screening of intestinal microflora for effective probiotic bacteria," *J. Agric. Food Chem.*, 49(4):1751–1760 (Apr. 2001).

Oyarzabal et al., "*In vitro* fructooligosaccharide utilization and inhibition of *Salmonella spp.* by selected bacteria," *Poult Sci.*, 74(9):1418–1425 (Sep. 1995).

Poupard et al., "Biology of the bifidobacteria," *Bacteriol Rev.*, 37(2):136–165 (Jun. 1973).

Pretlow, et al., "Aberrant crypts in human colonic mucosa: putative preneoplastic lesions," *J Cell Bio Chem Suppl.* 1992;16G:55–62.

Rammelsberg et al., "Antibacterial polypeptides of Lactobacillus species," *J. Appl. Bacteriol.*, 69:177–184 (1990).

Resnick et al., "Assessment of bifidobacteria as indicators of human fecal pollution," *Appl Environ Microbiol.*, 42(3):433–438 (Sep. 1981).

Rossi et al., "Improved cloning vectors for Bifidobacterium spp," *Lett. Appl. Microbiol.*, 26(2):101–104 (Feb. 1998).

Sambrook et al., *Molecular Cloning: A Laboratory Manual*, Cold Spring Harbor Laboratory Press, table of contents and title page; 26 pages (1989).

Sanders, "Probiotics," *Food Technol.*, 53:67–77 (1999).

Sasaki et al., "Enhanced resistance of mice to *Eschericia coli* infection induced by administration of peptidoglycan derived from *Bifidobacterium thermophilum*," *J Vet Med Sci.*, 56(3):433–437 (Jun. 1994).

Scardovi, "Genus Bifidobacterium Orla–Jensen 1924, 472$^{AL}$," In *Bergey's Manual of Systematic Bactgeriology*, vol. 2, Sneath et al., eds. ; Williams & Wilkins Co., Baltimore, MD, pp. 1418–1434 (1986).

Scardovi et al., "Deoxyribonucleic acid homology among the species of the genus Bifidobacterium isolated from animals," *Archiv fur Mikrobiologie*, 1970;72:318–325.

Shefet et al., "Efficacy of optimized nisin–based treatments to inhibit *Salmonella typhimurium* and extend shelf life of broiler carcasses," *J. Food Prot.*, 58(10):1077–1082 (1995).

Siegers et al., "Genes involved in immunity to the lantibiotic nisin produced by *Lactococcus lactis* 6F3," *Appl. Environ. Microbiol.*, 61(3):1082–1089 (Mar. 1995).

Singh et al., "*Bifidobacterium longum*, a lactic acid–producing intestinal bacterium inhibits colon cancer an modulates the intermediate biomarkers of colon carcinogenesis," *Carcinogenesis*. 1997 Apr.;18(4):833–41.

Steen et al., "Characterization of the nisin gene as part of a polycistronic operon in the chomosome of *Lactococcus lactis* ATCC 11454," *Appl. Environ. Microbiol.*, 57(4):1181–1188 (Apr. 1991).

Stevens et al., "Nisin treatment for inactivation of Salmonella species and other gram–negative bacteria," *Appl. Environ. Microbiol.*, 57(12):3613–3615 (Dec. 1991).

Torres et al., "Haem iron–transport system in enterohaemorrhagic *Escherichia coli* O157:H7," *Mol. Microbiol.*, 23(4):825–833 (Feb. 1997).

United States Department of Health & Human Services, "Nisin preparation: affirmation of GRAS status as a direct human food ingredient," *Federal Register*, 53(66): 11247–11251 (Apr. 1988).

United States Food and Drug Administration, Center of Food Safety & Applied Nutrition, Office of Premarket Approval, "Antimicrobial Food Additives—Guidance," retrieved Dec. 17, 2001 from the Internet. Internet URL: <http://www.cfsan.fda.gov/~dms/opa–antg.html>, 9 pages (Jul. 1999).

van der Meer et al., "Characterization of the *Lactococcus lactis* nisin A operon genes *nis*P, encoding a subtilisin–like serine protease involved in precursor processing, and *nis*R, encoding a regulatory protein involved in nisin biosynthesis," *J. Bacteriol.*, 175(9):2578–2588 (May 1993).

Woese et al., "Bacterial evolution," *Microbiol Rev.* 1987 Jun.;51(2):221–71.

Yamauchi et al., "Antibacterial activity of lactoferrin and a pepsin–derived lactoferrin peptide fragment," *Infect. Immun.*, 61(2):719–728 (Feb. 1993).

Yildirim et al. "Characterization and antimicrobial spectrum of bifidocin B, a bacteriocin produced by *Bifidobacterium bifidum* NCFB 1454," *J. Food Prot.*, 61(1):47–51 (Jan. 1998).

* cited by examiner

ISOLATED BIFIDOBACTERIA THAT PRODUCE SIDEROPHORES WHICH INHIBIT GROWTH OF *LACTOCOCCUS LACTIS*

CONTINUING APPLICATION DATA

This application claims the benefit of U.S. Provisional Application Ser. No. 60/212,273, filed Jun. 19, 2000, which is incorporated by reference herein.

BACKGROUND

Microbes have been used extensively as probiotics. The generally accepted definition for a probiotic is a live microbial feed supplement which beneficially affects the host animal by improving its intestinal microbial balance (Fuller, *J. Appl. Bacteriol.*, 66, 365–378 (1989)). The host animals targeted to date by commercially available probiotics include farm animals (including chickens, pigs, calves), pets (including dogs), and humans. While probiotics for farm animals have been commercially available since the 1960's, their market impact has been hampered by the use of antibiotics in animal feed and lack of knowledge on the probiotic mechanism of action (Fuller, In: *Probiotics: A Critical Review*, Tannock (ed),. Horizon Scientific Press, Norfolk, UK. pp. 15–2 (1999)). However, a resurgence of research interest in the probiotic field (and controversy surrounding antibiotics in animal feed) is now directing renewed interest in the animal probiotic market. The human probiotic market is also of vital importance to agriculture in the U.S. and other countries because of the association of human probiotics and dairy products. This association occurs because these microbes often survive best in dairy products and probiotics are presently delivered to consumers in the U.S. via milks and yogurts. The potential to use fruit juice sweetened dairy drinks for probiotic delivery, especially to children, is evident from the success of this approach in Europe and Asia. While the human probiotic market is quite significant in Europe and Asia, particularly Japan, it has only recently received attention by the U.S. food industry (Sanders, *Food Technol.*, 53, 67–77 (1999)). The growing U.S. interest in this market is primarily because of the increasing number of health-conscious consumers in the U.S. and the potential health benefits which are attributed to probiotics. The potential benefits include: increased resistance to gastrointestinal tract infections; alleviation of constipation; reestablishment of a healthy intestinal flora following antibiotic or chemotherapy treatments; stimulation of the immune system; reduction of serum cholesterol; prophylactic for intestinal cancers; and alleviation of the symptoms of lactose intolerance (reviewed in O'Sullivan et al., *Int. Dairy J.*, 8, 513–525 (1998); Sanders, *Food Technol.*, 53, 67–77 (1999)).

One type of probiotic is Bifibobacterium. Microbes representing the genus Bifidobacterium were first described by Tissier over one hundred years ago when studying the predominant microbes in the stools of breast fed infants. Tissier initially referred to these microbes as Bacillus and it was not until 1924 that the genus Bifidobacterium was proposed to classify these unique microbes. Their taxonomic position, however, remained in doubt throughout most of this century as many researchers thought they belonged in the genus Lactobacillus, primarily because of morphological and fermentative similarities (reviewed, Poupard et al., *Bacteriol Rev.*, 37, 136–165 (1973)).

Morphologically, bifidobacteria are rods of various shapes and often arranged in star-like or "V" patterns, typically called 'bifid' arrangements. They are nonmotile, nonspore forming and are strictly anaerobic (Scardovi, V. *Bergey's Manual of Systematic Bacteriology*, vol. 2., Sneath et al., (ed.) The Williams & Wilkins Co., Baltimore, Md., pp. 1418–1434 (1986)). The primary habitats of these microbes are the intestines of humans and many animals. Consequently, they are also found in sewage and, as a result, have been proposed as indicators of fecal contamination (Resnick et al., *Appl. Environ. Microbiol.*, 42, 433–438 (1981)). Their presence in the human intestine, primarily the large intestine, is almost universally accepted to be a contributing factor to a healthy well-being.

Production of Bacteriocins by Lactic Acid Bacteria, Including Bifidobacteria

The ability of lactic acid bacteria (LAB) to act as a preservative has been exploited in numerous dairy products for thousands of years. Their major preservative effect is due to the production of organic acids, primarily lactic acid. However, it is also known that many of them produce antimicrobial proteins, which have inhibitory properties against other related bacteria (Nes et al., *Antonie van Leeuwenhoek*, 70, 113–128, (1996)). All of the LAB bacteriocins characterized to date only inhibit certain Gram positive bacteria and exhibit no native activity against any Gram negative microbes. The range of activity against Gram positive bacteria varies with the bacteriocin. Some have a broad spectrum of activity such as nisin, which is produced by *Lactococcus lactis*, and has activity against most Gram positive bacteria (Hansen, *Crit. Rev. Food Sci. Nutr.*, 34, 69–93 (1994)). Others, such as Caseicin 80, which is produced by *Lactobacillus casei*, have activity only against strains of *L. casei* and possibly other closely related species (Rammelsberg and Radler, *J. Appl. Bacteriol.*, 69, 177–184 (1990)).

There have been a variety of reports indicating that bifidobacteria exhibit antibacterial action and this is primarily due to the production of lactic and acetic acids, which can inhibit the proliferation of pathogenic bacteria. Studies have indicated that bifidobacteria are effective at inhibiting the growth of *E. coli* (Ibrahim and Bezkorovainy, *J. Food Prot.*, 56, 713–715 (1993), Sasaki et al., *J. Vet. Med. Sci.*, 56, 433–437 (1994)), members of the genera Salmonella (Oyarzabal and Conner, *Poul. Sci.*, 74, 1418–1425 (1995), Gibson and Wang, *J. Appl. Bacteriol.*, 77, 412–420 (1994)), Listeria, Campylobacter, Shigella as well as *C. perfringens* and *Vibrio cholerae* (Gibson and Wang, *J. Appl. Bacteriol.*, 77, 412–420 (1994)). It has been suggested that bifidobacteria may be able to produce broad spectrum anti-microbial inhibitors, other than organic acids (Gibson and Wang, *J. Appl. Bacteriol.*, 77, 412–420 (1994)). However, there is not yet any convincing data published on the presence of any broad spectrum anti-microbial compound from bifidobacteria, other than organic acids. The only available evidence for a proteinaceous antimicrobial compound produced by a Bifidobacterium strain is the bacteriocin Bifidocin B from *B. bifidum* NCFB 1454, which is only active against certain Gram positive bacteria (Yildirim and Johnson, *J. Food Prot.*, 61, 47–51 (1998)).

Importance of Iron

With the exception of certain lactobacilli, all known microbes require iron for growth (Archibald, *FEMS Microbiol. Letts.*, 19, 29–32 (1983)). Because of the extreme insolubility of iron in aqueous solutions at neutral pH, it is generally a limiting factor for growth in most environments (Neilands et al.,. In: *Iron Transport in Microbes, Plants and Animals*, Winkelmann et al., (eds),. VCH, pp. 3–33 (1987)). Because iron plays such a central role in the metabolism of microbes, the expression of many cellular processes have become regulated by iron, making this element a global regulator of gene expression in microbes (Neilands, *Adv. Inorg. Biochem.*, 8, 63–90 (1990)). The primary functions that are regulated by iron in microbes are those involved in iron assimilation.

Dominant colonizers of an environment (especially environments of neutral pH) can have better iron scavenging systems and can inhibit the growth of other competing microbes by depriving them of iron (O'Sullivan, Ph.D thesis. National University of Ireland, Cork, 1990; O'Sullivan et al., *Microbiol Rev.*, 56, 662–676 (1992)). The human body also uses this concept as a natural defense to protect itself against pathogens. For example, the iron binding proteins transferrin and haem, which are present in blood, chelate iron making it biologically unavailable to microbes. However, successful pathogens can evolve and express receptors that enable them to use these host produced iron binding proteins as a source of iron, thus overcoming this natural defense. A recent example is *E. coli* O157:H7, a food borne pathogen that is characteristically associated with meat products, which was recently shown to have acquired the ability to use haem as an iron source (Torres et al., *Mol. Microbiol.*, 23, 825–833 (1997)).

Microbial iron uptake needs to be stringently controlled because excess iron is extremely toxic to microbes. Microbes acquire iron using either a low affinity system or a high affinity system. Microbes use the low affinity system in habitats of high bio-availability of iron. The low affinity system is essentially a regulatory system in the cell envelope to allow the controlled uptake of iron. In habitats of low bio-availability of iron, microbes need to employ a high affinity system to take up iron. This involves secreting an iron binding compound out of the cell to solubilize the iron and make it available to the cell. These compounds are generally called siderophores. Utilization of the iron-siderophore complex depends on the presence of a specific receptor on the cell envelope. This specific interaction is needed to prevent other competing microbes from using the complex. The current studies on iron metabolism by bifidobacteria indicated they did not secrete iron binding compounds and rely solely on a low affinity system to obtain iron (Bezkorovainy, In: Biochemistry and Physiology of Bifidobacteria, Bezkorovainy et al., (eds.), CRC Press, pp. 147–176 (1989)).

The concept of the use of microbes as probiotics has been around for nearly 100 years, yet its effect on human nutrition is still an emerging concept. Lack of convincing scientific validation for the efficacy of any ingested probiotic microbe on intestinal health has been a major reason for the low use of probiotics in human nutrition. Obtaining positive scientific validation requires the use of suitable probiotic. To date, selection of microbial strains for probiotic purposes has not been based on a scientific directed approach, primarily because it is not yet known what specific traits a desirable probiotic strain should possess. Filling this need will require the identification of specific traits of probiotics that cause a strain to be more useful as a probiotic than strains lacking the specific traits.

SUMMARY OF THE INVENTION

Prior to the present invention, the ability of bifidobacteria to secrete a siderophore had been investigated (Bezkorovainy In: Biochemistry and Physiology of Bifidobacteria, Bezkorovainy et al., (eds.), CRC Press, pp. 147–176 (1989)). It was concluded that bifidobacteria did not secrete a siderophore. In contrast, the present invention describes the unexpected and surprising observation that some bifidobacteria secrete a siderophore.

The present invention represents a significant advance in the identification of bifidobacteria that are useful as probiotics. The present invention also represents a significant advance in the art of compounds that prevent the acquisition of iron by microbes and the use of those compounds. It has been found that some strains of bifidobacteria isolated from the human intestine secrete compounds that prevent the acquisition of iron by microbes. The presence of these compounds inhibits the in vitro growth of microbes. Without intending to be limiting, it is expected that these compounds chelate iron. Bifidobacteria secreting these compounds will inhibit the growth of other microbes in the gastrointestinal tract, especially the large intestine, of animals. Moreover, these compounds will inhibit the growth of other microbes in, for instance, food and animal feed.

Accordingly, the present invention is directed to a method for inhibiting the replication of a microbe in the gastrointestinal tract of an animal, preferably a human. The method includes administering to an animal a Bifidobacterium that secretes a siderophore, and measuring the presence of the microbe in the gastrointestinal tract, preferably the large intestine. A decrease in the presence of the microbe in the animal after administration of the Bifidobacterium indicates inhibition of the replication of the microbe. The method can further include growing the Bifidobacterium under iron limited conditions before administration, preferably by growing the Bifidobacterium in the presence of an iron chelator. The microbe can be a prokaryotic microbe, including, for instance, *E. coli*, *Salmonella* spp., *Shigella* spp., *Campylobacter* spp., *Clostridium difficile*, or *Clostridium perfringens*.

The present invention is also directed to a method for treating a lactase deficiency. The method includes administering to an animal, preferably a human, a Bifidobacterium that secretes a siderophore, and detecting the presence of unabsorbed lactose in the gastrointestinal tract, preferably the large intestine. A decrease in the presence of unabsorbed lactose after administration of the Bifidobacterium indicates treatment of the lactase deficiency. The method can further include growing the Bifidobacterium under iron limited conditions before administration.

Another aspect of the present invention provides a method for establishing a Bifidobacterium flora in the gastrointestinal tract, preferably the large intestine, of an animal. The method includes administering to an animal a Bifidobacterium that secretes a siderophore, and measuring the presence of the Bifidobacterium in the gastrointestinal tract of the animal after administration. The method can further include growing the Bifidobacterium under iron limited conditions before administration. Preferably the animal is a human, including an immature infant, a premature infant, or a mature infant. The administration can occur after the human has undergone antibiotic therapy or chemotherapy.

The present invention also provides a method for preventing the replication of microbes in a food. The method includes adding to the food a Bifidobacterium that secretes a siderophore.

In another aspect, the present invention provides a method for decreasing the risk of colon cancer. The method includes administering to an animal a Bifidobacterium that secretes a siderophore, and detecting the presence of aberrant crypt foci in the colon of the animal. A lower number of aberrant crypt foci relative to an animal not administered the Bifidobacterium indicates a decrease in the risk of colon cancer.

The present invention is also directed to an isolated Bifidobacterium having the characteristics of strain RecB1, strain RecB4, strain J1, strain J2, strain J4, strain P1, strain 6A, or strain 10A.

The invention further provides a composition for inhibiting the replication of a microbe in the gastrointestinal tract of an animal, where the composition includes a Bifidobacterium that secretes a siderophore. Preferably, the Bifidobacterium is strain RecB1, strain RecB4, strain J1, strain J2, strain J4, strain P1, strain 6A, or strain 10A.

Also provided by the present invention is a method for obtaining a siderophore from a Bifidobacterium. The method includes incubating a Bifidobacterium under iron limited conditions, and isolating the siderophore. In another aspect, the invention includes a method for preparing a siderophore, including incubating a Bifidobacterium under iron limited conditions, and sterilizing the culture. The culture may be sterilized by removing essentially all water from the culture.

The invention also provides a method for decreasing the amount of free iron in a composition, including adding to a composition a siderophore, preferably, an isolated siderophore, obtained from a Bifidobacterium. In another aspect, the invention provides a method for inhibiting the replication of a microbe in a composition, including adding to a composition a siderophore, preferably, an isolated siderophore, obtained from a Bifidobacterium. In yet another aspect, the present invention provides a method for altering the expression of a siderophore in a Bifidobacterium. The method includes incubating under iron limited conditions a Bifidobacterium that does not secrete a siderophore, and selecting for a Bifidobacterium that replicates in the iron limited condition.

Further provided by the present invention is an isolated siderophore, preferably an isolated siderophore that binds $Fe^{2+}$, obtained from a Bifidobacterium, and a composition that includes a siderophore obtained from a Bifidobacterium, wherein the composition is sterile.

Definitions

As used herein, the term "microbe" refers to a prokaryotic microbe (including both gram positive and gram negative prokaryotic microbes, for instance, *E. coli*, Salmonella spp., Shigella spp., and Campylobacter spp.), eukaryotic microbe (including, for instance, yeast and other fungi), or a parasite (including multicellular eukaryotic parasites) that is introduced to an animal by the ingestion of food, and is capable of causing a disease in an animal.

As used herein, the term "animal" includes a member of the Class Aves or Mammalia, more preferably a chicken, pig, cow, horse, or human, most preferably a human.

As used herein, the term "replicate" refers the to ability of a microbe to grow or divide.

As used herein, the term "siderophore" refers to a compound that is secreted by a microbe and inhibits the replication of other microbes by depriving them of iron. Without intending to be limiting, it is expected that the siderophores secreted by the strains of the present invention bind iron. A siderophore can be a polypeptide, or other organic materials. A polypeptide refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

As used herein, an "immature infant" is one weighing about 500 grams to about 999 grams (about 17 ounces to about 2.2 pounds) at birth, usually before the twenty seventh week of gestation. As used herein, a "premature infant" is an infant typically born after the twenty seventh week and before full term and weighing about 1000 grams to about 2,499 grams (about 2.2 pounds to about 5.5 pounds) at birth. As used herein, a "mature infant" is an infant weighing at least about 2,500 grams (about 5.5 pounds) at birth, usually at or near full term.

As used herein, the term "Bifidobacterium flora" refers to the presence of a bifidobacteria in the gastrointestinal tract. A Bifidobacterium flora is considered to be established in an animal when there is, in increasing preference, at least about $10^6$, at least about $10^7$, at least about $10^8$, or at least about $10^9$ of the Bifidobacterium present per gram of feces.

As used herein, the term "antibiotic therapy" refers to a course of treatment of an animal with an antibiotic, typically to stop a microbial infection.

As used herein, the term "free iron" refers to iron, including ferrous iron and/or ferric iron, that can be used by an indicator microbe for growth. For instance, the iron is not bound to a siderophore or bound by an iron chelator like 2,2'-dipyridyl. An indicator microbe is a microbe that does not have the ability to remove iron from iron binding polypeptides such as transferrin or lactoferrin.

Unless otherwise specified, "a," "an," "the," and "at least one" are used interchangeably and mean one or more than one.

DETAILED DESCRIPTION OF PREFERRED EMBODIMENTS OF THE INVENTION

The present invention provides strains of the genus Bifidobacterium having the characteristics set forth in Table 1.

TABLE 1

Characteristics of the isolated bifidobacteria

| Strain designation | Iron dependent inhibition of indicator strains[1] |
|---|---|
| RecB1 | + |
| RecB4 | + |
| J1 | + |
| J2 | + |
| J4 | + |
| P1 | + |
| 6A[2] | + |
| 10A[3] | + |

[1]Indicator strains used were *Micrococcus luteus* ATCC 9341 and *E. coli* K12. "+" indicates the Bifidobacterium inhibits the growth of indicator strains.
[2]Previously referred to as Red1.
[3]Previously referred to as Red2.

The strains described in Table 1 can be isolated from individuals as described in Example 1. An "isolated" microbial strain means a strain has been removed from its natural environment (e.g., the gastrointestinal tract of an animal) and grown on media as a biologically pure culture. The ability to secrete a siderophore is not a characteristic shared by all bifidobacteria, as evidenced by the observation in Example 1 that only 8 of the 29 strains isolated secreted a siderophore.

A Bifidobacterium of the present invention is typically grown under certain conditions to secrete a siderophore. For instance, a Bifidobacterium is grown under iron limited conditions. As used herein, the phrase "iron limited conditions" refers to an environment, typically bacteriological media, that contains amounts of free iron that can inhibit the replication of an indicator microbe, for instance, *Micrococcus luteus* ATCC 9341, *E. coli* K12, *Lactococcus lactis*, or *Clostridium difficile*. Preferably, iron limited conditions are the result of the addition of an iron chelating compound to media. Examples of iron chelators include 2,2'-dipyridyl (also referred to in the art as α,α'-bipyridyl), 8-hydroxyquinoline, and ethylenediamine-di-O-hydroxyphenylacetic acid (EDDHA). Preferably, 2,2'-dipyridyl is used. Preferably, when Brain Heart Infusion (BHI, manufactured by Difco, Detroit, Mich.) is used, 2,2'-dipyridyl is added to the media at a concentration of, in increasing preference, at least about 0.3 mM, at least about 0.7 mM, at least about 1.1 mM, or at least about 1.5 mM.

During the anaerobic growth conditions of bifidobacteria in the gastrointestinal tract of an animal, the dominant form of iron is the ferrous form ($Fe^{2+}$). As the solubility of iron is pH dependent, the pH of the media used to grow a Bifidobacterium is preferably controlled. Preferably, the pH of the media is about pH 6.4 to about pH 7.5, more preferably, the pH of the media is about 7.0. This pH can be accomplished by the use of buffers known to the art. Alternatively, when certain media (e.g., BHI) is made for culturing a Bifidobacterium, additional carbohydrates are not added, as the catabolism of the carbohydrates can result in too much acid production by the Bifidobacterium.

The ability to secrete a siderophore can be measured by various methods, including testing the ability of the siderophore to inhibit the replication of a microbe that does not produce the siderophore. Such a microbe is referred to herein as an "indicator strain." The replication of an indicator strain is considered to be inhibited when the doubling time of the indicator strain on a particular media containing a siderophore is increased relative to the doubling time of the indicator on the same media not containing the siderophore. Preferably, the doubling time of the indicator strain is increased by at least about 10%, more preferably by at least about 50%. Most preferably, the doubling time of an indicator strain in the presence of a siderophore is undetectable.

The ability to secrete a siderophore can be measured by obtaining liquid from a culture of a bifidobacteria grown under conditions to produce the siderophore. For instance, a Bifidobacterium can be grown in liquid media and the bifidobacteria removed from the medium by, for instance, centrifugation. Alternatively, a Bifidobacterium can be grown on soft agar media (media supplemented with, e.g., about 0.75% agar) and then centrifuging the media after the Bifidobacterium has been removed. The bifidobacteria-free liquid can contain the siderophore, which can be added to a second media. The ability of an indicator strain to grow on the second media can then be determined Alternatively and preferably, the method includes measuring the ability of the secreted siderophore to inhibit growth of a microbial strain as described in Example 1. Useful indicator strains include for instance *Micrococcus luteus* ATCC 9341, *E. coli* K12, *Lactococcus lactis*, or *Clostridium difficile*.

It is expected that the ability to secrete a siderophore may be lost during prolonged culture in vitro. Accordingly, the strains of the present invention are preferably stored frozen in 15% glycerol from about −80° C. to about −70° C. Preferably, the medium used to store the frozen bifidobacteria is TYP medium (described below) supplemented with 15% glycerol.

The present invention provides methods for obtaining a siderophore from a Bifidobacterium, and compositions that include the siderophore. In some aspects, the siderophore is isolated. An "isolated" siderophore means the siderophore has been either removed from its natural environment, produced using recombinant techniques, or chemically or enzymatically synthesized. Preferably, methods for obtaining a siderophore from a Bifidobacterium include growing the Bifidobacterium in liquid medium. In initial experiments with commercially available media and other media known to the art, it was not possible to grow bifidobacteria such that the siderophore was produced; the sole method to produce the siderophore was to grow the Bifidobacterium on solid media. Further experimentation indicated that the buffering capacity of the media and the buffer used, and the time of incubation, were important to achieve production of the siderophore in liquid media. As expected, it was also beneficial to use a medium that contained little free iron, preferably, essentially no free iron.

Preferably, the conditions used to grow a bifidobacteria in liquid broth to express a siderophore include the first step of inoculating TYP medium. The bifidobacteria used to inoculate the TYP media can be obtained from a frozen stock, or can be a fresh isolate. Preferably, the bifidobacteria is obtained from a frozen stock. The TYP medium contains about 10.0 grams per liter (g/L) tryptone, about 5.0 g/L glucose, about 5.0 g/L soytone, about 2.5 g/L yeast extract, about 2.0 g/L $K_2HPO_4$, about 0.5 g/L cysteine HCl, about 0.5 g/L $MgCl_2$ $6H_2O$, about 0.25 g/L $ZnSO_4$ $7H_2O$, about 0.15 g/L $CaCl_2$ $2H_2O$, and about 1 milliliter Tween-80 per liter. The culture is incubated under anaerobic conditions without shaking for about 48 hours, at about 37° C.

The TYP medium containing the bifidobacteria is then used to inoculate a second medium. Preferably, a volume of the culture is removed from the TYP medium that is about 2% the final volume of the second medium. The second medium is prepared to minimize the amount of free iron present. For instance, the glassware used to prepare the medium is acid washed and rinsed in double distilled water ($ddH_2O$). The second medium contains about 20.0 g/L proteose peptone, about 1.5 g/L $K_2HPO_4$, about 1.5 g/L $MgSO_4$ $7H_2O$, about 5.0 g/L glucose, and about 100 millimolar (mM) of a biological buffer. Examples of biological buffers that can be used include piperazine-N,N'-bis(2-ethanesulfonic acid) (PIPES), 4-(2-hydroxyethyl)piperazine-1-ethanesulfonic acid (HEPES), and 3-morpholinopropanesulfonic acid (MOPS). Preferably, the biological buffer is PIPES. The medium is brought to 1 liter with $ddH_2O$ and brought to a pH of about 7.0 prior to autoclaving. After inoculation, the second medium is incubated under anaerobic conditions without shaking for about 37 hours at about 37° C.

The secreted siderophore in culture, preferably in liquid culture, can be used immediately in the methods described below without any further manipulation. Preferably, the culture is further treated to sterilize it. For example, the culture can be treated by exposure to conditions to kill the bifidobacteria present in the culture. Examples of conditions useful for sterilization include heat or ultraviolet radiation. The culture may be dried until essentially all moisture is removed and a powder containing the siderophore remains. Methods for drying cultures are known to the art and include, for instance, spray drying, freeze drying, tunnel drying, vacuum drying, and air drying. The result of such methods is a sterile mixture that includes a large number of components, including the siderophore. Optionally, the siderophore may be isolated. Isolation of the siderophore includes removal of the bifidobacteria by, for instance, centrifugation and/or filtration.

The present invention provides methods for using a Bifidobacterium that secretes a siderophore, and compositions including a Bifidobacterium that secrete a siderophore. Preferably the Bifidobacterium is one of the strains described herein. The Bifidobacterium can be administered as a biologically pure culture, or as a mixed culture. As used herein, a "mixed" culture is one containing a Bifidobacterium and at least one other microbe, preferably a prokaryotic microbe, more preferably a second Bifidobacterium. Bifidobateria that secrete a siderophore advantageously inhibit the growth of other microbes in vitro, and it is expected that siderophore-secreting Bifidobacterium will have the same effect on other microbes in the gastrointestinal tract of animals.

One method of the present invention provides inhibiting the replication of microbes in the gastrointestinal tract, preferably the large intestine, of an animal by administering to an animal a Bifidobacterium that secretes a siderophore. The method also includes measuring the presence in the gastrointestinal tract of the microbe to be inhibited, where a decrease in the presence of the microbe in the animal after administration of the Bifidobacterium indicates inhibition of the replication of the microbe in the gastrointestinal tract of the animal.

The presence of a microbe in the gastrointestinal tract, preferably the large intestine, can be monitored. When the microbe causes a disease, for instance diarrhea, the presence of the microbe in the gastrointestinal tract can be monitored by evaluating any change in the symptoms associated with the disease. Alternatively, the presence of a microbe in the gastrointestinal tract can monitored by collecting fresh fecal samples from the animal to which the Bifidobacterium was administered, homogenizing a predetermined amount of the sample in a buffer, and then adding a sample of the homogenate to a bacteriological medium appropriate for growing and detecting the microbe. For instance, if the microbe to be inhibited is an *E. coli*, an appropriate bacteriological medium would be MacConkey agar media. Typically, fresh fecal samples are collected over a period of time, for instance daily, weekly, or monthly, and the number of microbes present in the homogenate is monitored. Typically, at least one fecal sample is taken before the administration of the Bifidobacterium. Preferably, the number of microbes present in the homogenate is decreased by, in increasing order of preference, at least about 60%, at least about 70%, at least about 80%, most preferably at least about 90%.

The method can further include growing the Bifidobacterium under iron limited conditions before administration. Preferably, iron limited conditions include the growth of the Bifidobacterium on media containing an iron chelator. Preferably, the iron chelator is 2,2'-dipyridyl.

The types of microbes whose replication can be inhibited include those present in the gastrointestinal tract of an animal when the Bifidobacterium is administered (e.g., the method is therapeutic), and microbes that are introduced to the gastrointestinal tract after the Bifidobacterium is administered (e.g., the method is prophylactic). The prophylactic use of a Bifidobacterium can also be used in a method for inhibiting the establishment of a microbe in the gastrointestinal tract of an animal. Without intending to be limiting, examples of microbes that can be inhibited by the methods of the present invention include prokaryotic microbes (including, for instance, gram negative microbes and gram positive microbes), eukaryotic microbes (including, for instance, yeast and other fungi), and parasites (including multicellular eukaryotic parasites). Preferably, the microbe to be inhibited causes an intestinal disease, i.e., the microbe is a pathogen. Examples of intestinal disease include diarrhea and bowel bacterial overgrowth. Microbes causing intestinal disease include, for instance, enterotoxigenic *E. coli*, enteropathogenic *E. coli*, enterohaemorrhagic *E. coli*, Campylobacter jejuni, Yersinia entercolitica, Shigella spp., Salmonella spp., *Clostridium difficile, Clostridium perfringens, Vibrio cholera, Giardia lamblia, Entamoeba histolytica*, Helicobacter spp., Listeria spp., and Mycobacteria. Typically, microbes causing intestinal disease are initially introduced to an animal via food ingested by the animal, and are referred to as food borne pathogens.

Another aspect of the present invention is directed to preventing the replication of microbes in a food item so that the Bifidobacterium acts as a food preservative. The method includes adding to the food a Bifidobacterium that secretes a siderophore. Preferred foods include low acid foods, including for instance, milk, meats, and vegetables. Preferably, the types of microbes inhibited by a Bifidobacterium that secretes a siderophore include *E. coli*, Salmonella spp., or Clostridium spp.

The present invention provides methods for treating disaccharidase deficiency, preferably congenital or acquired lactase deficiency. The method includes administering to an animal a Bifidobacterium that secretes a siderophore. Preferably, the Bifidobacterium produces the enzyme beta-galactosidase. The method also includes measuring the presence in the gastrointestinal tract of unabsorbed lactose. Microbial fermentation of the unabsorbed lactose results in increased hydrogen production, which can be measured in exhaled air by methods known to the art, including for instance, gas chromatography. A decrease in the amount of hydrogen in exhaled air by an animal after administration of a Bifidobacterium relative to the amount of hydrogen in exhaled air before administration indicates the treatment of lactase deficiency. The method can further include growing the Bifidobacterium under iron limited conditions before administration. The present invention also provides methods for decreasing the symptoms associated with disaccharidase deficiency, preferably congenital or acquired lactase deficiency. Symptoms associated with lactase deficiency include hydrogen production, and osmotic diarrhea.

Another aspect of the present invention is directed to methods for establishing a Bifidobacterium flora in an animal. Such a flora is expected to competitively inhibit the ability of other microbes to establish themselves as a flora in the gastrointestinal tract. The method includes administering to an animal a Bifidobacterium that secretes a siderophore. The method also includes measuring the presence in the gastrointestinal tract of the Bifodobacterium over a period of time following the administration. A Bifidobacterium flora is considered to be established in an animal when there is at least about $10^6$ of the Bifidobacterium present per gram of feces. The method can further include growing the Bifidobacterium under iron limited conditions before administration. Preferably, the animal is an adolescent or adult human or an infant, including an immature, premature, or mature infant. The present method can be used to establish a Bifidobacterium flora in a healthy human, and in humans that have had their normal intestinal flora modified by, for instance, diarrhea or by drug treatment including antibiotic therapy or chemotherapy.

The present invention further provides methods for decreasing the risk of colon cancer. The formation of aberrant crypt foci in the colon is recognized as an index of colon cancer risk, and animal models are known to the art that can be used to test for the ability of a Bifidobacterium to decrease the formation of aberrant crypt foci in the colon (see, for instance, Singh et al., *Carcinogenesis,* 18, 833–841 (1997)). The method includes administering to an animal a Bifidobacterium that secretes a siderophore, and detecting the presence of aberrant crypt foci in the colon of the animal. A lower number of aberrant crypt foci relative to an animal not administered the Bifidobacterium indicates a decreased risk of colon cancer. The method can further include growing the Bifidobacterium under iron limited conditions before administration.

Administration of the bifidobacteria used in the methods of the present invention is oral. It is well known to the art that bifidobacteria can be incorporated into different types of foods and beverages. In particular, the bifidobacteria of the present invention can be incoporporated into solid and semi-solid dairy products, including fermented dairy products, for instance yogurt. Other examples of dairy products include cottage cheese, cheese, and powdered milk. Bifidobacteria can also be incorporated into baby foods. Beverages to which bifidobacteria can be added include milk, vegetable juice, fruit juice, soy milk, soybean milk, fermented soybean milk, and fruit flavored dairy beverages.

Administration can also be by ingestion of encapsulated bifidobacteria. For instance, encapsulation may allow better survival of the probiotic in the food or beverage, or may allow better delivery of the probiotic to the large intestine. Bifidobacteria can also be incorporated into tablet form.

Bifidobacteria can also be dried, for instance, freeze-dried, in the presence of a stabilizer to protect viability. Freeze dried preparations can be added to a food or a beverage by the consumer.

The invention further provides methods of using a siderophore, preferably an isolated siderophore, obtained from a bifidobacteria. In general, the siderophore acts as a bacteriostatic agent that has the effect of preventing the growth of microbes by reducing the level of free iron available to the microbes. It has been observed that siderophores produced by bifidobacteria bind ferrous iron ($Fe^{2+}$), which is prevalent under anaerobic conditions; however, it has also been observed that bifidobacteria siderophores also act as bacteriostatic agents in aerobic conditions. This was unexpected and surprising since the predominant form of iron present in aerobic conditions is ferric iron ($Fe^{3+}$), which siderophores produced by bifidobacteria do not appear to bind.

The siderophores of the present invention can be used to decrease the amount of free iron present in a composition. Examples of compositions to which the siderophore can be added include animal feeds, and foods and beverages including, for instance, whey, cheeses including low acid cheeses, and the other foods and beverages described herein. The presence of the siderophore will act as a bacteriostatic agent and inhibit the replication of microbes in the composition and thereby increase food safety and prolong shelf life. The siderophore that is added to the composition can be present in a sterile mixture, for instance, a powder or a liquid. Preferably, the siderophore that is added to the composition is isolated.

The present invention is also directed to a method for altering the expression of a siderophore in a Bifidobacterium. It has been observed that after extensive in vitro culture, bifidobacteria can lose the ability to express a siderophore. The ability to express a siderophore can be selected for by incubating on medium containing low levels of free iron a Bifidobacterium that does not express a siderophore. Preferably, the Bifidobacterium is incubated on media containing gradually increasing amounts of an iron chelator. For instance, the initial concentration of an iron chelator like 2,2'-dipyridyl can be about 1 mM. The Bifidobacterium is then exposed to increasing concentrations of the iron chelator until the strain is able to grow on medium containing greater than about 3 mM 2,2'-dipyridyl. At the end of this process, bifidobacteria that can grow in the presence of an iron chelator express a siderophore. Bifidobacteria selected in this way can be used in the methods described herein.

The present invention is illustrated by the following examples. It is to be understood that the particular examples, materials, amounts, and procedures are to be interpreted broadly in accordance with the scope and spirit of the invention as set forth herein.

EXAMPLE 1

Strain Isolation Procedure

All strains were isolated essentially as described in Kullen et al. (*FEMS Microbiol Lett.*, 154, 377–383 (1997)). Briefly, all human subjects participating were not consuming or had consumed, for at least 4 months, products containing bifidobacteria. The 18–35 year old, healthy, non-smoking subjects had no histories of gastrointestinal disorders nor had they used antibiotics in the previous year. Fresh fecal samples were collected from the subjects on the premises and immediately homogenized in an appropriate amount of sterile peptone water (0.1%). The homogenate was transferred to an anaerobic chamber, where it was serially diluted and plated on BIM-25 (Muñoa et al., *Appl. Environ. Microbiol.*, 54, 1715–1718 (1988)). After anaerobic incubation at 37° C., red colonies were randomly selected. The authenticity of the colonies appearing on the BIM-25 plates was verified by assessing the activity of fructose-6-phosphate phosphoketolase, a diagnostic enzyme for bifidobacteria. Only those expressing functional fructose-6-phosphate phosphoketolase were used in the following studies. A total of 29 strains were isolated by this procedure.

Selected strains were subsequently speciated using a molecular analysis of the 16s rRNA gene or the recA gene as described by Kullen et al. (*FEMS Microbiol Lett.*, 154, 377–383 (1997)). The strains isolated by this procedure were designated RecB1, RecB4, J1, J2, J4, P1, 6A (previously referred to as Red1), and 10A (previously referred to as Red2).

EXAMPLE 2

Methodology for Detecting Siderophore Production by Bifidobacteria

The procedure used was to grow the bifidobacteria strains on a standard 0.45 μm nitrocellulose filter placed onto of a BHI agar plate (Difco, BD Biociences, Sparks, Md.), and also on a BHI plate with 0.3 mM 2,2'-dipyridyl. 2,2'-dipyridyl is an iron chelator that depletes the bioavailability of iron in the medium. This is specifically a ferrous ($Fe^{2+}$) chelator, which was chosen as $Fe^{2+}$ is the dominant form of soluble iron during anaerobic conditions. Additional glucose was not added to prevent excess growth and acid production. Following incubation at 37° C. for 48 hours under anaerobic conditions, the filters containing the bifidobacteria cells were removed, and the plates were sprayed with an indicator strain. In some experiments, instead of spraying the indicator strains onto the plate, an indicator strain was added to liquid soft agar media and then poured over the plate on which a bifidobacteria strain had been grown. The indicator strains used included *Micrococcus luteus* ATCC 9341 and *E. coli* K12. Spraying was done using a perfume sprayer which was acid and ethanol washed prior to use. *M. luteus* was grown in BHI media supplemented with 0.3 mM 2,2'-dipyridyl, and *E. coli* was grown in BHI media supplemented with 0.3 mM 2,2'-dipyridyl. After adding the indicator strain by spraying, plates were then incubated at conditions suitable for growth of the indicator. For *M. luteus*, these were 30° C., aerobically for about 24 hours. For *E. coli*, these were 37° C., aerobically for about 24 hours.

The *M. luteus* and *E. coli* indicator strains grew well on the entire surface of the plates that did not contain the siderophore. In contrast, on eight of those plates containing the iron chelator, there was a large zone of inhibition around the area on which the filter containing the bifidobacteria had been incubated. These results indicated that eight strains of bifidobacteria (i.e., the eight strains identified in Example 1) produced a diffusible compound that inhibited the growth of the indicator strains, and that this compound was preferentially produced during incubation in low iron conditions. To further test if the inhibition was dependent on low iron conditions, the solution containing the indicator strains was fortified with iron prior to spraying. Under these conditions no inhibition zone was detected, suggesting the inhibition by the compound was due to iron competition.

One strain of Bifidobacterium, RecB1, was chosen for further analysis. The ability of this strain to inhibit other bacteria was determined using the inhibition test described above. RecB1 was able to inhibit the growth of *Lactococcus lactis, Clostridium difficile,* and *Clostridium perfringens.* This inhibition was blocked by the addition of iron. Thus, the inhibition was due to iron competition.

EXAMPLE 3

Production of Siderophore by Bifidobacteria Grown in Liquid Media

To achieve production of the siderophore in a broth medium, a bifidobacteria strain is first inoculated from stock into TPY broth media and allowed to grow without shaking for 48 hours at 37° C. under anaerobic conditions. The stock of the bifidobacteria is in TPY medium supplemented with 15% glycerol, and stored at −70° C. TPY medium is as follows:

| | |
|---|---|
| tryptone (Difco, Detroit, MI) | 10.0 grams/liter (g/L) |
| glucose (Mallinckrodt Baker, Paris, KY) | 5.0 g/L |
| soytone (Difco, Detroit, MI) | 5.0 g/L |
| yeast extract (BentonDickinson, Cockeysville, MD) | 2.5 g/L |
| $K_2HPO_4$ (Fischer Scientific, Pittsburgh, PA) | 2.0 g/L |
| cysteine HCl (Fischer Scientific, Pittsburgh, PA) | 0.5 g/L |
| $MgCl_2$ $6H_2O$ (Mallinckrodt Baker, Paris, KY) | 0.5 g/L |
| $ZnSO_4$ $7H_2O$ (Fischer Scientific, Pittsburgh, PA) | 0.25 g/L |
| $CaCl_2$ $2H_2O$ (Mallinckrodt Baker, Paris, KY) | 0.15 g/L |
| Tween-80 (Fischer Scientific, Pittsburgh, PA) | 1 ml |
| water to 1 liter. | |

After 48 hours anaerobic growth at 37° C., the culture was sub-inoculated at 2% into the following medium, which was developed to be as iron free as possible. The composition of the medium is as follows:

| | |
|---|---|
| proteose peptone (Difco, Detroit, MI) | 20.0 g/L |
| $K_2HPO_4$ (Fischer Scientific, Pittsburgh, PA) | 1.5 g/L |
| $MgSO_4$ $7H_2O$ (Mallinckrodt Baker, Paris, KY) | 1.5 g/L |

-continued

| | |
|---|---|
| glucose (Mallinckrodt Baker, Paris, KY) | 5.0 g/L |
| piperazine-N,N'-bis(2-ethanesulfonic acid) (PIPES free acid) (ICN Biomedicals, Inc., Aurora, OH) | 100 millimolar (mM). |
| double distilled water ($ddH_2O$) to 1 liter. | |

The medium is prepared in acid (HCl) washed glassware, followed by rinsing with $ddH_2O$. After adding $ddH_2O$ to 1 liter, the pH of the medium is brought to 7.0 by the addition of sodium hydroxide. The medium is sterilized by autoclaving at 121° C. for 15 minutes.

Following inoculation, the culture was incubated anaerobically without shaking at 37° C. for 37 hours. An aliquot of the medium was removed and the bifidobacteria removed by centrifugation. The medium was then tested for the presence of a siderophore using the test described in Example 2.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition consisting essentially of an isolated Bifidobacterium that secretes a siderophore that inhibits growth of a *Lactococcus lactis*.

2. A composition comprising an isolated Bifidobacterium that secretes a siderophore that inhibits growth of a *Lactococcus lactis*, wherein the composition comprises substantially no free iron, comprises an iron chelator, or a combination thereof.

3. A composition comprising an isolated Bifidobacterium that secretes a siderophore which inhibits growth of a *Lactococcus lactis*, and a food wherein said composition is substantially free of iron, comprises an iron chelator, or a combination thereof.

4. A method for establishing a Bifidobacterium flora in the gastrointestinal tract of an animal comprising administering to an animal a composition comprising an isolated Bifidobacterium that secretes a siderophore that inhibits the growth of *Lactococcus lactis*, wherein the composition comprises substantially no free iron, comprises an iron chelator, or a combination thereof, and measuring the presence of the Bifidobacterium in the gastrointestinal tract of the animal after administration.

5. The method of claim 4 further comprising growing the Bifidobacterium under iron limited conditions before administration.

6. The method of claim 4 wherein the gastrointestinal tract is the large intestine.

7. The method of claim 4 wherein the animal is a human.

8. The method of claim 7 wherein the human is an infant selected from the group consisting of an immature infant, a premature infant, and a mature infant.

9. The method of claim 7 wherein the administration occurs after the human has undergone antibiotic therapy.

10. The method of claim 7 wherein the administration occurs after the human has undergone chemotherapy.

11. A method for preventing the replication of microbes selected from the group consisting of *Lactococcus lactis, Clostridium difficile* and *Clostridium perfringens* in a food, the method comprising adding to the food a composition comprising an isolated Bifidobacterium that secretes siderophore that inhibits growth of *Lactococcus lactis*, wherein the composition comprises substantially no free iron, comprises an iron chelator, or a combination thereof.

12. A method for obtaining a secreted siderophore that inhibits the growth of *Lactococcus lactis* from an isolated Bifidobacterium, the method comprising incubating the isolated Bifidobacterium under iron limited conditions, and isolating the siderophore.

13. A method for inhibiting the replication of a microbe selected from the group consisting of *Lactococcus lactis, Clostridium difficile* and *Clostridium perfringens* in the gastrointestinal tract of an animal, comprising administering to an animal a composition comprising an isolated Bifidobacterium that secretes a siderophore that inhibits growth of *Lactococcus lactis*, wherein the composition comprises substantially no free iron, comprises an iron chelator, or a combination thereof, and measuring the presence of said microbe that was present in the gastrointestinal tract of the animal prior to administration, where a decrease in the presence of the microbe in the animal after administration of the Bifidobacterium indicates inhibition of the replication of the microbe.

14. The method of claim 13 further comprising growing the Bifidobacterium under iron limited conditions before administration.

15. The method of claim 14 wherein growing the Bifidobacterium under iron limited conditions comprises growth in the presence of an iron chelator.

16. The method of claim 13 wherein the animal is a human.

17. The method of claim 13 wherein the gastrointestinal tract is the large intestine.

18. A method for inhibiting the replication of a microbe selected from the group consisting of *Lactococcus lactis, Clostridium difficile* and *Clostridium perfringens*, in a composition, the method comprising adding to the composition a secreted siderophore that inhibits the growth of *Lactococcus lactis* obtained from an isolated Bifidobacterium.

* * * * *